US007494771B2

(12) United States Patent
Picard et al.

(10) Patent No.: US 7,494,771 B2
(45) Date of Patent: Feb. 24, 2009

(54) UNIVERSAL METHOD AND COMPOSITION FOR THE RAPID LYSIS OF CELLS FOR THE RELEASE OF NUCLEIC ACIDS AND THEIR DETECTION

(75) Inventors: Francois J. Picard, Cap-Rouge (CA); Christian Menard, St.-Lambert-de-Levis (CA)

(73) Assignee: Geneohm Sciences Canada, Inc., Sainte-Foy, Quebec ( * ) Notice: Subject to any disclaimer, the term of this patent is extended or adjusted under 35 U.S.C. 154(b) by 221 days.

(21) Appl. No.: 10/466,583

(22) PCT Filed: Jul. 19, 2002

(86) PCT No.: PCT/CA02/01088

§ 371 (c)(1),
(2), (4) Date: Dec. 8, 2003

(87) PCT Pub. No.: WO03/008945

PCT Pub. Date: Jan. 30, 2003

(65) Prior Publication Data

US 2004/0076990 A1  Apr. 22, 2004

Related U.S. Application Data

(60) Provisional application No. 60/306,163, filed on Jul. 19, 2001.

(51) Int. Cl.
*C12Q 1/68* (2006.01)
*C12N 1/06* (2006.01)

(52) U.S. Cl. .......................................... 435/6; 435/259

(58) Field of Classification Search ........................ None
See application file for complete search history.

(56) References Cited

U.S. PATENT DOCUMENTS

| 4,295,613 | A |   | 10/1981 | Moore et al. |  |
|---|---|---|---|---|---|
| 5,374,522 | A | * | 12/1994 | Murphy et al. | 435/6 |
| 5,376,527 | A |   | 12/1994 | Robson et al. |  |
| 5,464,773 | A |   | 11/1995 | Melendez et al. |  |
| 5,567,050 | A |   | 10/1996 | Zlobinsky et al. |  |
| 5,643,767 | A |   | 7/1997 | Fischetti et al. |  |
| 5,942,425 | A | * | 8/1999 | Walters et al. | 435/173.7 |
| 5,994,066 | A |   | 11/1999 | Bergeron et al. |  |
| 6,448,002 | B1 | * | 9/2002 | Hillebrand et al. | 435/6 |
| 2001/0012612 | A1 | * | 8/2001 | Petersen et al. | 435/5 |

FOREIGN PATENT DOCUMENTS

| WO | WO 00/05338 | 2/2000 |
|---|---|---|
| WO | WO 01/23604 | 4/2001 |

OTHER PUBLICATIONS

Ruske et al. Small Scale DNA Sample Preparation Method for Field PCR Detection of Microbial Cells and Spores in Soil; Applied and Environmental Microbiology, vol. 64, No. 7 (1998) pp. 2463-2472.*

Kaufman et al. Molecular and Cellular Methods in Biology and Medicine; 1995. pp. 9-10.*

Cole-Parmer Catalog 2003-2004, p. 1041.*

Bélanger et al., Apr. 2002, "Rapid Detection of Shiga Toxin-Producing Bacteria in Feces by Multiplex PCR with Molecular Beacons . . . ", J Clin Microb, 4:1436-1440.

Belgrader et al. (1999), "A Minisonicator To Rapidly Disrupt Bacterial Spores for DNA Analysis", Anal. Chem. 71:4232-4236.

Bergeron et al., 2000, "Rapid Detection of Group B Streptococci in Pregnant Women at Delivery", The New England Journal of Medicine 343:175-179.

Boom et al. 1990, "Rapid and Simple Method for Purification of Nucleic Acids", J. Clin. Microbiol., 28:495-503.

Comejo et al., 1998, "Comparison of $C_{18}$-Carboxypropylbetaine and Glass Bead DNA Extraction Methods for Detection . . . ", Appl. Env. Microbiol. 64:3099-3101.

Drake et al., 1996, "Differentiation of *Lactobacillus helveticus* strains using molecular typing methods", Food Res. Int. 29:451-455.

Jaffe et al. 2000, "Rapid Extraction from and Direct Identification in Clinical Samples of Methicillin-Resistant *Staphylococci* Using the PCR", J. Clin. Microbiol., 38:3407-3412.

Ke et al., 2000 "Development of Conventional and Real-Time PCR Assays for the Rapid Detection of Group B *Steptococci*", Clinical Chemistry 46:324-331.

Kessler et al. 1997,"Rapid Detection of *Mycoplasma pneumoniae* by an Assay Based on PCR and Probe Hybridization in a . . . ", J. Clin. Microbiol. 35: 1592-1594.

Kuske et al. 1998 "Small-Scale DNA Sample Preparation Method for Field PCR Detection of Microbial Cells and Spores in Soil", Appl. Environ. Microbiol. 64 2463-72.

Martineau et al. 1998 "Species-Specific and Ubiquitous-DNA-Based Assays for Rapid Identification of *Staphylococcus aureus*", J. Clin. Microbiol. 36:618-623.

Martineau et al., 2000 "Multiplex PCR assays for the detection of clinically relevant antibiotic resistance genes in *staphylococci* . . . ", J. Antimicrob. Chemother. 46:527-533.

Meier et al. 1993, "Elimination of Contaminating DNA with Polymerase Chain Reaction Reagents: Implications for a General Approach . . . ", J. Clin. Microbiol. 31:646-652.

(Continued)

*Primary Examiner*—Jon P Weber
*Assistant Examiner*—Paul C. Martin
(74) *Attorney, Agent, or Firm*—Knobbe Martens Olsen & Bear LLP

(57) ABSTRACT

This invention describes a rapid (10 to 15 minutes), simple, flexible and efficient method of nucleic acids extraction for nucleic acid testing assays. This method has the following basic steps: i) mechanical cell lysis using solid particles in the presence of a chelating agent, followed by ii) controlling the presence and/or activity of NAT assays inhibitors. This method is applicable to various biological samples and universal for microorganisms, as one can use it to extract nucleic acids from test samples containing target viruses, bacteria, bacterial spores, fungi, parasites or other eukaryotic cells, including animal and human cells.

45 Claims, No Drawings

OTHER PUBLICATIONS

Miller et al.1999, "Evaluation and Optimization of DNA Extraction and Purification Procedures for Soil and Sediment Samples", Appl. Env. Microbiol. 65:4715-4724.

Nikaido, H. "Outer Membrane", In: *Escherichia coli* and *Salmonella*, Cellular and Molecular Biology 1996, 2nd Ed., vol. 1, Chapter 5, ASM Press, Washington, pp. 29-47.

Sargeant et al. 1998 "Clinical mastitis in dairy cattle in Ontario: Frequency of ocurrence and bacteriological isolates", Can. Vet J. 39:33-38.

Singer-Sam et al. 1989, "Use of Chelex to Improve the PCR Signal From a Small Number of Cells", Amplifications 3:11.

Swan et al. 1999, "Human Papillomavirus (HPV) DNA Copy Number Is Dependent on Grade of Cervical Disease and HPV Type", J. Clin. Microbiol. 37:1030-1034.

Templeton et al. 2001, "The detection of *Chlamydia trachomatis* by DNA amplification methods in urine samples from men with urethritis", Int. J. of STD & AIDS,12:793-796.

Toye et al. 1998, "Inhibition of PCR in Genital and Urine Specimens Submitted for *Chlamydia trachomatis* Testing", J. Clin. Microbiol., 36:2356-2358.

Van Burik et al. 1998 "Panfungal PCR Assay for Detection of Fungal Infection in Human Blood Specimens", J. Clin. Microbiol. 36:1169-1175.

Wilson, I.G. 1997, "Inhibition and Facilitation of Nucleic Acid Amplification", Applied Env. Microbiol., 63:3741-3751.

Yoshimi et al. 1993, "One step procedure of PCR-DNA extraction from paraffin-embedded materials by Chelex®—100", Acta Pathol. Jap. 43:790-791.

Dion et al. 1999 "Comparison of nine commercial kits for rapid nucleic acid extraction from microbial cultures", The 99th ASM General Meeting, Abstract C-481.

Medias: "Impact Glass Beads" Pruduct Information, Online! 2000.

Martineau et al. 2000, "Development of a Rapid PCR Assay Specific for *Staphylococcus saprophyticus* and Application . . . ", J. Clin. Microb. 38:3280-3284.

\* cited by examiner

UNIVERSAL METHOD AND COMPOSITION FOR THE RAPID LYSIS OF CELLS FOR THE RELEASE OF NUCLEIC ACIDS AND THEIR DETECTION

CROSS-REFERENCE TO RELATED APPLICATIONS

This application claims priority of International Patent Application PCT/CA02/01088, filed on 19 Jul. 2002, and U.S. provisional patent application 60/306,163, filed on 19 Jul. 2001.

BACKGROUND OF THE INVENTION

Classical Methods for the Isolation of Nucleic Acids from Microorganisms

With the advent of molecular biology, an increasing number of diagnostic methods are based on the detection of nucleic acids. Nucleic acid amplification technologies represent useful tools in molecular biology. Since the discovery of the polymerase chain reaction (PCR), various protocols have been described for isolating nucleic acids suitable for detection and identification of microorganisms. However, most of these protocols are time-consuming and often require the use of toxic chemicals. In addition, protocols need to be tailor-made for each microbe type; a lysis protocol for fungi may not be suitable for gram-negative bacteria, or parasites, or bacterial spores, and so on. Furthermore, these protocols require numerous steps, increasing the risk of sample-to-sample or carry-over contamination.

Hugues et al. (Methods in Microbiology, 1971, vol. 5B, Academic Press, New York) have reviewed the available methods for disintegrating microbes for preparing biologically active fractions. The method selected will depend on its capability to process samples of a certain size or to be able to process multiple samples in a reasonable period of time, while the desired nucleic acids retain their integrity. Classical physical methods of cell breakage include mechanical cell disintegration (crushing and grinding, wet milling, ultrasonics, hydraulic shear, freeze pressure), liquid or hydrodynamic shear (French press, Chaikoff press, homogenizers, wet mills, vibration mills, filters, ultrasonic disintegration) and solid shear (grinding, Hugues press). Chemical methods of cell disintegration are mostly aimed at modifying the cell wall or cytoplasmic membrane, or both, so that the cells either become leaky or burst due to the effects of turgor pressure. Methods include osmosis, drying and extraction, autolysis, inhibition of cell wall synthesis, enzymic attack on cell walls, bacteriophages and other lytic factors, and ionizing radiation.

Several methods of cell disruption, with or without solid particles, and involving physical agitation to release nucleic acids have been described. Examples include a cell disrupter from Amoco (U.S. Pat. No. 5,464,773) and the FastPrep® apparatus from Qbiogene (U.S. Pat. No. 5,567,050). However, no examples of reduction into practice were provided in those patents. Other commercial devices that may be used to lyse cells using similar shaking-type bead mills include the Micro-Dismembrator II from B. Braun Biotech (Allentown, Pa., USA) and the Mini-BeadBeater from BioSpec (Bartlesville, Okla., USA). However, most methods described in the literature using this type of apparatus require additional nucleic acid purification steps after the lysis step (Miller et al., 1999, Appl. Env. Microbiol. 65: 4715-4724; Cornejo et al., 1998, Appl. Env. Microbiol. 64: 3099-3101). In addition, most protocols rely on the presence of lysogenic chemicals to enhance mechanical cell lysis. A major drawback of these methods is that the chemicals used often adversely affect subsequent molecular biology processes, such as the detergent sodium dodecyl sulfate (SDS) in PCR.

Significant progress has been made in the last few years by manufacturers to improve the simplicity of release and purification of nucleic acids from microorganisms present in clinical specimens. However, for laboratory personnel, it is not obvious to make a choice in the plethora of commercially available nucleic acids extraction kits. Those kits exhibit variable performances in the preparation of various test samples containing diverse target microorganisms for nucleic acids testing (NAT). These kits have different total nucleic acids recovery, number of manipulation steps and time requirements. Example 2 shows a comparison of 8 different commercially available DNA extraction kits with the method described in this invention. The conclusion was that with regards to speed, total recovery of DNA and number of manipulation steps, the sample preparation method described below was the best protocol.

A Novel Extraction Method that is Simple, Rapid, Universal and Versatil

The method described in this invention is a Rapid Universal Cell Lysis and Nucleic Acids Preparation (RUCLANAP) protocol. It requires approximately 10 to 15 min, in a simple, flexible and efficient protocol. The main sequence of events underlying this invention are an initial mechanical cell lysis using solid particles in the presence of a chelating agent, followed by a control of substances inhibitory to polymerases as used in amplification reactions, or inhibitory to other steps of NAT assays. Said inhibitory substances are present in the test sample and/or are released upon cell lysis into the lysate. For most applications, no further purification of nucleic acids is required. Such a control can be effected by diverse ways such as heating, adsorbing, freezing, removing or diluting the NAT inhibitors in the sample or the lysate. The advantages of this method are simplicity, rapidity, efficiency, universality (effective with all microbial species)and low cost. Prior to the present invention, heat was used to lyse cells (U.S. Pat. No. 5,376,527), agitation with particles was used to lyse cells (U.S. Pat. Nos. 5,567,050 and 4,295,613, and PCT Publication No. WO 02/10333), agitation with particles in organic solvents was used to lyse cells (U.S. Pat. No. 5,643,767), and agitation with particles was applied to already heat-lysed cells to provide access to nucleic acids (U.S. Pat. No. 5,942,425). Prior to the present invention, the particular sequence of events (agitation with particles in chelating buffer followed by heat inactivation of PCR inhibitors) was applied to prepare DNA for molecular biology. However, in these earlier methods, cell lysis did not rely upon mechanical forces, but mainly on beat provided by a boiling step. For example, others have used the combination of a vortexing step in CHELEX®, a weak ion-exchange matrix, followed by boiling of the sample (Kessler et al., 1997, J. Chin. Microbiol. 35: 1592-1594; Drake et al., 1996, Food Res. Int. 29: 451-455; Yoshimi et al., 1993, Acta Pathol. Jap. 43: 790-791). In all cases, the very short vortex step was performed only to mix the CHELEX® ion-exchange matrix with the sample in order to sequester divalent cations, and bind compounds which inhibit PCR (Singer-Sam et al., 1989, Amplifications 3:11); while cell lysis was obtained during the heating step, a process that is not universal for all microbes, especially bacterial spores and yeasts cells. As revealed in this invention in Example 19, the heating steps during the PCR protocol are not sufficient to lyse *Mycobacterium smegmatis*.

Patent publication WO 99/15621 describes a method for mechanically lysing bacteria or yeasts wherein a liquid sample comprising the bacteria or yeasts is placed in a container with particles having 90-150 μm, namely 100 μm for bacteria and the large ones having 400-600 μm, namely 500 μm for yeasts. This method is not optimal, since after 8 minutes of vortex, about 60% of S. epidermidis and C. albicans are lysed.

Patent publication WO 00/05338 discloses a <<magnetic>> vortex method for lysing cells. At least two sizes of particles are used to mechanically break the cells. The larger particles are composed of a material which respond to a magnetic field (iron, namely), while the smaller ones are non-magnetic beads. The large beads are placed in movement by actuating a magnetic device and the sample is crushed between the large and the small beads, the smaller being moved by the larger ones. The ratio of size between the small beads and the target cells is rather small (50/1) while the ratio of size between the large and small beads is relatively large (40/1). The large beads have therefore the function of crushing the target cells between them and the small beads to free the cell contents into the lysate solution. Further, this application only provides a <<qualitative>> appreciation of the lysis rate and of the integrity of the nucleic acids obtained therefrom. Only electrophoretic gels show the results of the process. Amplification process further performed on nucleic acids are very sensitive processes which require a high level of lysis liability and reproducibility. WO 00/05338 is totally silent on achieving this high standard with the disclosed <<magnetic>> vortex method.

Patent publication WO 02/10333 describes a method which may be adapted for different techniques: sonication, mechanical vortex and magnetic vortex. The method comprises at least three parameters selected from: a) 50-100% of particles mass with regards to the total mass of the sample to be treated, b) a ratio of particles of a small diameter to particles of a large diameter (when two sizes of particles are used) which is less than or equal to 50%, c) a lysis duration of 9 to 20 minutes, d) glass beads that are involved in the motion of the particles and not in the lysis per se which are in a number of less than 7; and e) iron beads that have the same role as in d) but for a magnetic vortex, which are in a number of 5 to 15. Again the lysing particles have the size as in WO 99/15621 (the small ones having 90-150 μm, namely 100 μm for bacteria and the large ones having 400-600 μm, namely 500 μm for yeasts). Larger particle size ratios are favoured when a mixture of particles sizes is used (more than 50%), along with a relatively long lysis duration. Except for sonication, the other agitation techniques require large non-lysing particles which are present to put the small particles into motion. These big particles may render the bead matrix more voluminous and bumpy at the interface with the lysate, increasing the dead volume, and hence rendering the recovery by pipetting of the latter more difficult.

A publication by Jaffe et al. (J. Clin. Microbiol., 2000, 38: 3407-3412) discloses the use of 1.0 g of 100 μm glass beads and 0.25 g of CHELEX-100™ ion-exchange matrix in a volume of 0.5 ml of bacterial sample to mechanically break cells and release nucleic acids, further followed by a heating step. The process which is called "Bead beating with Chelex" however lacks sensitivity towards certain species, namely methicillin-resistant S. aureus (MRSA) even if the sensitivity is acceptable for other bacteria easier to break up, such as gram-negative species. There is no suggestion in this reference to vary the size of beads to improve the sensitivity and the versatility ("universality") of the method for recovering efficaciously nucleic acids from any microorganism. Furthermore, this method has not been tested with clinical samples.

During the 99$^{th}$ ASM General Meeting held in Chicago in 1999, (Abstract C-481), the present inventors have disclosed the results of a comparative study conducted with the present method and kit ("then referred to as the IDI DNA extraction kit") with eight other kits (see Example 2). No details were given on the protocol for lysing the cells and the components involved therein.

The RUCLANAP method is universal for microorganisms, as one can use it to extract nucleic acids from viruses, bacteria, bacterial spores, fungi, parasites or from other eukaryotic cells, including animal and human cells. The basic RUCLANAP protocol is versatile, as it can easily be adapted, depending on the type of clinical sample used, in order to dilute or concentrate the microorganisms present in the sample, and/or to extract crude nucleic acids, and/or to control (inactivate, adsorb, dilute or remove) sample-specific inhibitors of NAT assays (Wilson, Applied Env. Microbiol., 1997, 63:3741-3751). For genetic analysis of RNA, RNase inhibitors may be added to the sample before nucleic acid extraction with RUCLANAP; no additional purification of total RNA is necessary for subsequent amplification and detection, such as with RT-PCR (see Example 18).

The applications for this method are numerous: the samples from which microbial nucleic acids have been successfully prepared using this method include microbial broth cultures, positive blood cultures, suspensions of microbial colonies grown on agar media, as well as a variety of biological samples including blood, plasma, platelet concentrates, urine, cerebrospinal fluid, amniotic fluid, meconium, wound exudate, stools, nasal swabs, throat swabs, anal swabs, vaginal swabs, vaginal/anal swabs, rectal swabs, and bovine milk. The efficiency of Streptococcus agalactiae lysis by the RUCLANAP method was estimated to 99.99%, as determined by viable counts (see Example 5). For detailed sample preparation protocols with various specimens, see Examples 2 to 12, 15, and 17-20. The method is also amendable to scaling up or down, and automation.

One concern in the handling of biological specimens is safety. Heating of a clinical sample containing infectious agents is one of the preferred methods to render samples safer for handling. U.S. Pat. No. 5,376,527 describes a lysis-effective amount of heat that is sufficient to render difficult-to-lyse cells of Mycobacterium tuberculosis non-infectious. We have found that the combination of the cell lysis step and the heating step of the RUCLANAP method also renders most clinical samples safer for handling. A heating and/or freezing step may be performed prior to RUCLANAP to render test samples safer for handling.

SUMMARY OF THE INVENTION

It is an object of the present invention to provide a universal method and composition or kit for the rapid preparation of nucleic acids from cells, namely microbial cells or viruses, said method comprising:

A. Placing biological samples in the presence of a granulometric gradient formed by solid particles having nominal diameter sizes comprised between 75 μm and 200 μm;

B. Submitting said mixture to sufficient mechanical forces to disrupt cell walls and membranes, to release cellular and sub-cellular (mitochondria) contents further submitted to a step of controlling the presence and/or activity of inhibitors of NAT assays.

Namely, the particles have nominal diameter sizes higher than 100 μm and lower than 1500 μm. In a preferred embodiment, the particles essentially consist of a nominal diameter size varying from 150 to about 1200 μm, namely more than 150 μm and lower than or equal to 1180 μm.

In a further preferred embodiment, the solid spherical particles are acid-washed glass beads of diameter of two ranges: one from 150 to 212 μm, and another one from 710 to 1180 μm. For universal cell (bacteria, yeasts, fungi, parasites, animal and human cells) or virus lysis, the beads are preferably mixed in a 4:1 ratio (w/w), and there is a total of 0.05 g of glass bead matrix per 1.5 mL microtube. Other bead ratios are also possible; for example, to lyse yeast cells, the beads are preferably mixed in a 1:1 ratio (w/w) or higher, and there is about 0.02 g of glass bead matrix per 1.5 mL microtube. When virus particles are also a target for lysis, a third range of about 75 to 106 μm may be added, if necessary or desirable.

In another preferred embodiment, the biological sample and particles are in a buffered solution containing chelating agents.

In a further preferred embodiment, said buffered solution consists of 10 mM Tris-HCl (pH 8.0), and chelating agent is 1 mM EDTA.

In another preferred embodiment, the mechanical forces used are produced by a device using horizontal orbital motion with or without a recessed platform (e.g. model Genie2 vortex from Fisher Scientific, Nepean, Ont., Canada), set to level 7, for 5 min.

In the above embodiments, there is no need for large particles (of the millimeter diameter size order) not involved in the lysis but involved in the motion of the lysing particles, such as those described in WO 99/15621, WO 00/055338 and WO 02/10333. Instead of these non-lysing larger size particles, the present inventors have used a mixture comprising granulometric gradients of small particles and large particles of comparatively bigger sizes (≈150-212 μm and 710-1180 μm). That mixture allows the user to be capable of performing a lysis step per se within 5 minutes and without recourse to any mechanical aid such as non-lysing big particles (larger than about 2 mm diameter size).

In a further preferred embodiment, the mechanical forces are produced by a device using vertical angular motion (e.g. FastPrep® FP-120 apparatus from Qbiogene, Carlsbad, Calif., USA), set at power level 6 for 45 seconds.

In another embodiment, said forces used to disrupt cells in the presence of solid particles are transmitted by ultrasounds.

In order to control the inhibitors of NAT assays, one of the preferred embodiments is heating the mix at temperatures ranging from about 55 to 100° C. for a sufficient time.

In another preferred embodiment, the lysis medium would also comprise a material binding or adsorbing NAT assays inhibitors, such as activated carbon (charcoal, activated charcoal). This component would be added or would be part of the bead mixture and would comprise different particle sizes, coarse synthetic beads coated with carbon, or aggregated porous carbon beads. Those substances allow to adsorb porphyrin and porphyrin-like pigments or derivatives, hemin and hemin-like molecules, steroids and steroid-like hormones which are all known to be inhibitors of NAT assays.

The NAT assays inhibitors may also be controlled simply by diluting the sample, or by removal on density gradients, such as PERCOLL™ density gradient media, or on adsorbent media (charcoal, etc.), or by freezing the sample. Combination of means or steps for controlling NAT assays inhibitors are also within the scope of the present invention (for example, heat+gradient, or heat+dilution, etc.)

DETAILED DESCRIPTION OF THE INVENTION

The Rapid Universal Cell Lysis and Nucleic Acids Preparation (RUCLANAP) method described in this invention forms the core of protocols used to prepare nucleic acids suitable for molecular diagnostic applications based on nucleic acid detection. Modifications may be added depending on the nature of the test sample processed (see Examples below), demonstrating the versatility of the method.

The sample of interest is first resuspended in a buffered solution which also includes a chelating agent. Tris (tris[hydroxymethyl]-aminomethane) is the preferred buffer here, since in addition to its buffering power, Tris also contributes to the weakening of the lateral interaction between lipopolysaccharide (LPS) molecules in bacterial cell walls, by partially replacing other cations tightly bound to LPS. However, other buffers well known to biochemists could be used instead. Even no buffer at all may be appropriate, as many sample types are naturally buffered; also, in some cases the assay may not require a high sensitivity of detection. The chelating agent is preferably EDTA (ethylenediaminetetraacetate), which chelates divalent cations, hence inhibiting nuclease enzymes by sequestering their essential metallic cofactors; yet, other metal chelating agents could also be used instead. An additional effect of chelation is the loss of cations involved in neutralization of the electrostatic repulsion between LPS molecules, resulting in the destabilization of the LPS monolayer portion of the membrane. The observed increase in cell permeability is likely to be due to the filling in of the space, formely occupied by LPS, by phospholipid molecules, thereby creating phospholipid bilayer domains (*Escherichia coli* and *Salmonella*: Cellular and Molecular Biology, 1996, $2^{nd}$ Ed., Vol. I, Chapter 5, ASM Press, Washington).

The mixture is then put in contact with solid particles. The preferred volume of said mixture is 10 to 500 μL. Alternatively, said particles may already be present in the solution containing the chelating agent. Preferred solid particles consist of sterile, acid-washed glass beads placed into a 1.5-mL microtube. Solid particles could be a mixture of particles having different sizes. The preferred mixture consists of two size ranges of beads, the first ranging from 150 to 212 μm (70-100 U.S. sieve), and the second from 710 to 1180 μm (16-25 U.S. sieve). Although in general small beads (150 to 425 μm) are efficient to lyse bacterial cells, efficient lysis of yeast cells requires larger beads (710 μm and up). Therefore, beside separate kits, compositions and methods tailored for one particular type of microorganism, we devised a universal lysis mix, in which the two size ranges of beads are mixed in a 4:1 ratio (w/w) and the total weight of beads is 0.05 g per microtube. This mix can efficiently lyse yeast cells (see Example 2). Alternatively, in the yeast lysis mix, the two size ranges of beads are mixed in a 1:1 ratio (w/w) for a total weight of 0.02 g of beads per microtube. Other particles found to be suitable for cell lysis include (but are not limited to) Ottawa sand and zirconia beads.

Without being bound to any theory, we believe that using a granulometric gradient of particles having diameter sizes ranging from 75 to about 2000 μm (namely 75 to 1500, even 75 to 1200) permits better lysis. This is attributable to the presence of particles of various different sizes (the gradient) which increase the potential collisional surfaces to favor cell disruption and reduce the dead volume, hence facilitating the recovery of the lysate. For the universal lysis of different microorganisms, having various sizes and shapes as bacteria and yeast have, we discovered that combining two non-contiguous granulometric gradients (150 to 212 μm and 710 to 1180 μm) was particularly efficient and convenient (see Example 1). Mixing what others called large non-lysing particles (WO 99/15621, WO 00/055338 and WO 02/10333) with a gradient of smaller lysing particles may also be used with the present invention.

Next, the viral, bacterial, fungal, parasitical, animal or human nucleic acids are released upon cell disruption by mechanical action. The latter could be provided by applying horizontal orbital motion (vortexing) on the microtube using a model Genie2 vortex from Fisher Scientific, for 1 to 5 min at power level 7. An alternate way to break cells is to use the FastPrep® FP120 apparatus from Qbiogene, set at power level 6 for 45 seconds. Other devices, including ultrasound generators, may be suitable to apply sufficient mechanical energy to break cells.

The final step involves the control or neutralization of potential inhibitors of NAT assays, by heating the preparation. The temperature used may vary from 55 to 100° C., but preferably, the protocol uses 95° C. The heating time may vary from a few seconds to 15 min, depending on the sample, the usual duration being 2 to 5 min. Although heat is not absolutely required for some types of samples, a universal protocol would preferably include this step for maximum performance of the nucleic acids extraction.

Depending upon the nature of the sample, purification or concentration or dilution steps can be added either before or after lysis of the cells. Said steps may include, but are not limited to: buoyant density separation (with PERCOLL™ density gradient media for instance, as described in Examples 4, 9 and 10), filtration, ultrafiltration, centrifugation and/or washing, ultracentrifugation, solid phase adsorption on carbon or other adsorbent material, chromatography, capture on magnetic particles, freezing, etc. All these steps intend to control the inhibitors of NAT assays frequently present in biological samples. Freezing of the RUCLANAP-treated specimen has been shown to improve sensitivity in some cases; freezing is known to circumvent inhibition of nucleic acid amplification (Toye et al., 1998, J. Clin. Microbiol., 36:2356-2358; Templeton et al., 2001, Int. J. of STD & AIDS, 12:793-796).

The duration of agitation, and the ratios between the volume of the beads, the total volume of the sample and the total volume of the recipient are all parameters that may be adapted depending on the chosen agitation technique (magnetic, mechanical, sonicating). Examples of strategies to optimize lysis with particles may be found in WO 99/15621, WO 00/05338 and WO 02/10333. Optimization may also be performed for a given type of recipient and agitation technique, by monitoring the efficiency of lysis and the sensitivity of the NAT assay conducted afterwards.

Unless specified otherwise, the contents of the cited references are incorporated to the present text by simply referring thereto.

LIST OF EXAMPLES

EXAMPLE 1: Core protocol for the RUCLANAP.
EXAMPLE 2: Comparison of RUCLANAP with eight commercial kits for rapid DNA extraction from microbial cultures.
EXAMPLE 3: Use of RUCLANAP for detection of Shiga toxin-producing bacteria.
EXAMPLE 4: Preparation of platelet concentrates for PCR amplification using RUCLANAP.
EXAMPLE 5: Use of RUCLANAP for the detection of group B streptococci in anal, vaginal, and combined vaginal/anal specimens.
EXAMPLE 6: Application of RUCLANAP for direct detection of *S. saprophyticus* from urine samples.
EXAMPLE 7: Detection of *Candida albicans, Escherichia coli* and *Staphylococcus aureus* in blood samples.
EXAMPLE 8: RUCLANAP for extraction of human DNA from clinical samples.
EXAMPLE 9: Effect of RUCLANAP on *Bacillus subtilis* endospores.
EXAMPLE 10: Detection of bacteria in bovine milk using RUCLANAP.
EXAMPLE 11: Use of RUCLANAP for the detection of *Staphylococcus aureus* in nasal swabs.
EXAMPLE 12: Direct detection of vancomycin-resistant enterococci from fecal samples using RUCLANAP.
EXAMPLE 13: Effect of variations in the ratios of glass beads sizes, or in total weight of beads, on RUCLANAP.
EXAMPLE 14: The effect of the particle size on lysis efficiency.
EXAMPLE 15: Effect on PCR of potentially inhibitory substances present in anal/vaginal samples.
EXAMPLE 16: Effect of bacterial density on RUCLANAP.
EXAMPLE 17: Total RNA extraction from *Escherichia coli* using RUCLANAP.
EXAMPLE 18: Extraction of genomic DNA from *Cryptosporidium parvum* using RUCLANAP.
EXAMPLE 19: Extraction of genomic DNA from *Mycobacterium smegmatis* using RUCLANAP.
EXAMPLE 20: RNA extraction from HIV-1 using RUCLANAP.
EXAMPLE 21: Use of zirconia beads for RUCLANAP.

EXAMPLES

Example 1

Core protocol for the RUCLANAP. The sample (e.g. microbial cells recovered from an overnight broth culture after centrifugation, or microbial colonies grown on agar media, or microbial cells recovered from a clinical sample) is resuspended in a buffered solution (10 to 50 mM Tris-HCl, pH 8.0) which also includes a chelating agent (1 to 25 mM EDTA). The mixture (usually 10-100 μL) is then transferred to a 1.5-mL, screw-capped conical microtube (VWR Scientific Products, Mississauga, Ont., Canada) containing sterile, acid-washed glass beads. There are two sizes of beads, the first ranging from 150 to 212 μm (cat. no. G1145, Sigma, St-Louis, Mo., USA), and the second from 710 to 1180 μm (cat. no. G1152, Sigma). In the universal lysis mix, the two types of beads are mixed in a 4:1 ratio (w/w) and the total weight of beads is 0.05 g per microtube; whereas in the yeast lysis mix, the beads are mixed in a 1:1 ratio (w/w) for a total weight of beads of 0.02 g per microtube.

Next, the viral, bacterial, fungal, parasitical, animal or human nucleic acids are released when cells are disrupted by mechanical action. The latter is provided by vortexing the microtube on a model Genie2 vortex from Fisher Scientific, for 1 to 5 min at power level 7. An alternate way to break cells is to use the FastPrep® FP120 apparatus from Qbiogene set at power level 6 for 45 seconds.

The final step involves the neutralization of potential inhibitors of NAT assays by heating the preparation. The temperature used may vary from 55 to 100° C., but preferably, the protocol uses 95° C. The heating time may vary from 1 to 15 min, the usual duration being 2 to 5 min.

Using this protocol, we were able to extract nucleic acids suitable for PCR amplification from a variety of microorganisms, including: *Bacillus cereus, B. subtilis* (vegetative cells and endospores), *B. anthracis* (vegetative cells, endospores and germinating spores), *Candida albicans, Candida dubliniensis, Candida krusei, Candida parapsilosis, Candida tropicalis Clostridium difficile, Corynebacterium accolens, Corynebacterium genitalium, Corynebacterium jeikeium, Corynebacterium kutscheri, Corynebacterium minutissimum, Corynebacterium striatum, Crytosporidium parvum, Enterobacter cloacae, Enterococcus faecalis, Enterococcus faecium, Escherichia coli*, human immunodeficiency virus 1 (HIV-1), *Klebsiella oxytoca, Klebsiella pneumoniae, Methanobrevibacter smithii, Micrococcus luteus, Mycobacterium smegmatis, Porphyromonas gingivalis, Porphyromonas gulae, Pseudomonas aeruginosa, Salmonella choleraesuis, Schizosaccharomyces pombe, Serratia marcescens, Shigella dysenteriae, Staphylococcus aureus, Staphylococcus epidermidis, Staphylococcus saprophyticus, Streptococcus agalactiae, Streptococcus mitis, Streptococcus mutans, Streptococcus parauberis, Streptococcus pneumoniae, Streptococcus pyogenes, Streptococcus salivarius, Streptococcus sanguinis*, and *Yersinia enterocolitica*.

Nucleic acids extracted using RUCLANAP remain stable for several months when stored frozen at −80° C. or −20° C., and may be freeze-thawed repeatedly (see Examples 3, 5, 11 and 12). Depending on the starting sample, DNA preparations from clinical samples can be used for PCR amplification in the next 24 h when stored at 4° C. (see Example 5), while DNA preparations from microbial cultures, stored at 4° C., can be used for up to one week. In all the above storage conditions, no significant loss in PCR sensitivity has been observed.

Example 2

Comparison of RUCLANAP with eight commercial kits for rapid DNA extraction from microbial cultures. Eight commercial kits for rapid DNA isolation from microbial cultures were compared with the method described in the present invention. We have verified the efficiency of these kits to prepare DNA from the following microorganisms: (i) *E. coli* ATCC 25922 (gram-negative bacterium), (ii) *E. faecium* ATCC 19434 and *S. aureus* ATCC 25923 (gram-positive bacteria) and (iii) *C. albicans* ATCC 56884 (fungus). Broth cultures in mid-log phase of growth ($OD_{600}$ of around 0.5 for bacteria and 0.8 for fungi) were used as test samples.

Nine methods were thus evaluated by comparing their capacity to extract DNA suitable for PCR from the four different microorganisms. The following DNA extraction methods were executed according to manufacturers instructions:
  K1: Fast RNA™ blue Kit from Qbiogene;
  K2: Dynabeads® DNA DIRECT™ from Dynal Biotech (Lake Success, N.Y., USA);
  K3: NUCLISENS™ nucleic acid purification system from Organon Teknika (bioMerieux, Marcy l'toile, France);
  K4: GeneReleaser™ from BioVentures Inc (Murfreesboro, Tenn., USA);
  K5: High Pure™ PCR Template preparation Kit from Roche (Basel, Switzerland);
  K6: Instagene™ Matrix from Bio-Rad Laboratories (Mississauga, Ont., Canada);
  K7: QIAamp® Tissue Kit from Qiagen (Mississauga, Ont., Canada);
  K8: Fast DNA™ Kit from Qbiogene;
  K9: RUCLANAP.

The RUCLANAP protocol used for this experiment is described in Example 1, using the following conditions: chelating buffer=5×TE (50 mM Tris-HCL, pH 8.0, 5 mM EDTA); glass beads=universal lysis mix; mechanical action=vortex at speel level 7 for 5 minutes. Few minor modifications of the original kit protocols were made in order to facilitate comparison between the different methods. These modifications were: (i) a volume of 100 μL of bacterial culture in mid-log phase was always used with each method, and (ii) the final volume of the DNA preparation was always adjusted to 100 μL. DNA extracts yielded with each method were serially diluted to reach equivalents of 105 to 1 genome copy/μL.

Conserved regions of the bacterial 16S rRNA or fungal, 18S rRNA genes were used as targets for the amplification of DNA from bacteria or *C. albicans*. The 16S rRNA primers were described in our previous patent (SEQ ID NOs. 126 and 127, U.S. Pat. No. 5,994,066), whereas the 18S rRNA primers were described in the literature (van Burik et al., 1998, J. Clin. Microbiol. 36: 1169-1175). Amplification reactions were performed in a 20 μL reaction mixture containing 50 mM KCl, 10 mM Tris-HCl (pH 9.0), 0.1% Triton X-100, 2.5 mM $MgCl_2$, 0.4 μM each of the two selected PCR primers, 200 μM each of the four deoxynucleoside triphosphates, 0.5 U Taq DNA polymerase (Promega, Madison, Wis., USA) combined with TaqStart™ antibody (Clontech Laboratories Inc., Palo Alto, Calif., USA). Elimination of contaminating nucleic acids potentially present in the reagent mixture was carried out as described in the literature (Meier et al., 1993, J. Clin. Microbiol. 31: 646-652). One μL of diluted nucleic acid preparation was transferred into 19 μL of reaction mixture and was subjected to thermal cycling (3 min at 94° C., and then 30 cycles of 30 sec at 95° C. for the denaturation step, 30 sec at 55° C. for the annealing step, and 30 sec at 72° C. for the extension step, followed by a final extension step of 2 min at 72° C.) using a DNA engine PTC-200™ thermal cycler (MJ Research Inc., Waltham, Mass., USA).

Ten μL of the PCR-amplified reaction mixture was analyzed by electrophoresis at 170 V for 30 min, in a 2% agarose gel containing 0.5 μg of ethidium bromide per mL. The size of the amplification products was estimated by comparison with a 50-bp molecular size standard ladder.

As shown in Table 1, the highest efficiency for DNA recovery was obtained with K9 (the RUCLANAP method described in the present invention), followed in order by K1, K5, K7, K6, K3, K8, K2, and K4. The difference in efficiency between kits ranged from 0.5 to 4 log, depending on the microbial species tested. When analyzed on the basis of manipulation steps and time requirement, the most convenient kit was K9, requiring 15 min in a 5 step protocol, followed by K2, K6, K1, K8, K4, K5, K3, and K7. These extraction methods required 15 to 150 min for completion, in 4 to 40 steps protocols. Overall, the most efficient and simplest method for rapid DNA extraction from microbes was RUCLANAP.

Example 3

Use of RUCLANAP for detection of Shiga toxin-producing bacteria. This assay was published in the Journal of Clinical Microbiology, 2002, 4:1436-1440. No information regarding the sample preparation protocol was disclosed in this publication. Shiga toxin-producing *Escherichia coli* and *Shigella dysenteriae* cause bloody diarrhea and haemolyticuremic syndrome. Currently, identification relies mainly on the phenotypic identification of *S. dysenteriae* and *E. coli* serotype O157:H7. However, other serotypes of *E. coli* are increasingly found to be producers of type 1 and/or type 2 Shiga toxins. Two pairs of PCR primers targeting highly conserved regions present in each of the Shiga toxin genes stx1 and stx2 were designed to amplify all variants of those genes (described in our previous patent publication WO 01/23604). The first primer pair, oligonucleotides SEQ ID NO. 1080 and 1081, yields an amplification product of 186 bp from the stx1 gene. For this amplicon, the molecular beacon SEQ ID NO. 1084 (patent publication WO 01/23604) was designed for the specific detection of stx1 using the fluorescent label 6-carboxy-fluorescein. A second pair of PCR primers, oligonucleotides SEQ ID NO. 1078 and 1079, yields an amplification product of 160 bp from the stx2 gene. Molecular beacon SEQ ID NO. 1085 (patent publication WO 01/23604) was designed for the specific detection of stx2 using the fluorescent label 5-tetrachloro-fluorescein. Both primer pairs were combined in a multiplex PCR assay.

Stool samples were prepared in the following manner. For solid fecal material, a sterile swab was dipped into the sample, then transferred to a 1.5-mL screw-capped microtube containing 1 mL of TE buffer (10 mM Tris-HCl, 1 mM EDTA). The stem of the swab was wrapped in gauze and bent until it broke, so that the microtube, containing the inoculated portion of the swab, could be closed. Fecal material was resuspended in solution by vortexing vigourously at least 15 seconds. A 50 µL aliquot was transferred to a 1.5-mL, screw-capped microtube containing 0.05 g of sterile, acid-washed glass beads (universal lysis mix, as described in Example 1). For liquid fecal material, a 50 µL aliquot of liquid stools was transferred directly to the microtube containing beads. Subsequently, the microtube was vortexed for 5 min at speed level 7 on a Genie2 model vortex from Fisher Scientific. After a quick centrifuge spin, the microtube was heated for 5 min at 95° C. A 2 min. centrifugation at 10 000 g followed. The supernatant was transferred to another microtube, and 1.5 µL of 1:10 and 1:20 dilutions were used in PCR reactions. Extracts could be stored for at least one week at −20° C. without any significant loss in PCR analytical sensitivity.

PCR amplification was carried out using 0.8 µM of each primer SEQ ID NO. 1080 and 1081, 0.5 µM of each primer SEQ ID NO. 1078 and 1079, 0.3 µM of each molecular beacon, 8 mM $MgCl_2$, 490 µg/mL bovine serum albumin (BSA), 0.2 mM dNTPs (Amersham Biosciences, Uppsala, Sweden), 50 mM Tris-HCl, 16 mM $NH_4SO_4$, 1× TaqMaster (Eppendorf, Hamburg, Germany), 2.5 U KlenTaq1 DNA polymerase (AB Peptides, St. Louis, Mo., USA) coupled with TaqStart™ antibody (Clontech), and 1.5 µL of the prepared stool sample in a final reaction volume of 25 µL. PCR amplification was performed using a SmartCycler® thermal cycler (Cepheid, Sunnyvale, Calif., USA). The optimal cycling conditions for maximum sensitivity and specificity were 60 seconds at 95° C. for initial denaturation, then 45 cycles of three steps consisting of 10 seconds at 95° C., 15 seconds at 56° C. and 5 seconds at 72° C. Detection of the PCR products was made in real-time, by measuring the fluorescent signal emitted by the molecular beacon when it hybridizes to its target at the end of each annealing step at 56° C.

The assay was specific for the detection of both toxins, as demonstrated by the perfect correlation between PCR results and the phenotypic characterization performed using antibodies specific for each Shiga toxin type. The assay was successfully performed on several Shiga toxin-producing strains isolated from various geographic areas of the world, including 10 O157:H7 *E. coli*, 5 non-O157:H7 *E. coli* and 4 *S. dysenteriae*. The detection limit for this PCR assay was around $10^5$ colony forming units (CFU) per gram of fecal material. The assay was validated by testing 38 fecal samples obtained from 27 patients. Of these samples, 26 were positive for stx1 and/or stx2. Compared with the culture results, both the sensitivity and the negative predictive value were 100%. The specificity was 92% and the positive predictive value was 96%. RUCLANAP worked efficiently with both liquid or solid stools, and whether or not they contained traces of blood.

Example 4

Preparation of Platelet Concentrates for PCR Amplification Using RUCLANAP. Blood platelet preparations need to be monitored for bacterial contaminations, as the latter may develop during storage. Primers were designed from tuf gene fragments. Oligonucleotide sequences conserved for the 17 major bacterial contaminants of platelet concentrates were chosen (oligonucleotides SEQ ID NO. 636, 637, 553 and 575, described in our previous patent publication WO 01/23604, yielding amplification products of 245 bp and 368 bp), thereby permitting the detection of these bacterial species. The 104 bacterial species whose genomic DNA is detected efficiently with the assay are listed in Table 14 of our previous patent publication WO 01/23604.

Detection of these PCR products was made on the LightCycler™ thermocycler (Roche) using SYBR® Green I (Molecular Probes Inc., Eugene, Oreg., USA), a fluorescent dye that binds to double-stranded DNA.

Platelet concentrates (250 µL), spiked with each of the 17 major bacterial contaminants, were submitted to buoyant density separation over 600 µL of PERCOLL™SIM-40 (40% PERCOLL™ density gradient media (Amersham Biosciences) and 60% peptone water (BD Microbiology Systems, Cockeysville, Md., USA)) in a 1.5 mL screw-capped microtube containing glass beads (universal lysis mix, see Example 1). The mixture was centrifuged 75 seconds at 16 200 g. The supernatant was removed, and the pellet was mixed by inversion with 1 mL of 0.01 M phosphate-buffered saline (PBS), pH 7.4. After centrifugation at 10 000 g for 5 min, the supernatant was removed, and the pellet was resuspended in 20 µL of TE or ultrapure water. Cells were disrupted in the FASTPREP® FP-120 apparatus (Qbiogene) for 45 seconds at power level 6. After a quick spin, the microtube was heated 2 mm at 95° C. One µL of each preparation was used for PCR amplification.

Fluorogenic detection of PCR products with the LightCycler™ was carried out using 1.0 µM of each universal primer and 0.4 µm of each *Staphylococcus*-specific primer, 4.5 mM $MgCl_2$, 0.4 mg/mL BSA, 0.2 mM dNTPs (Amersham Biosciences), PC2 buffer (50 mM Tris-HCl, 3.5 mM $MgCl_2$, BSA 0.15 mg/mL, 16 mM $NH_4(SO_4)_2$); 1.875 U KlenTaq DNA polymerase (AB Peptides) coupled with TaqStart™ antibody (Clontech), and 0.5×SYBR® Green I (Molecular Probes, Inc.); in a final volume of 15 µL. Elimination of contaminating nucleic acids potentially present in the reagent mixture was carried out as described above. The optimal cycling conditions for maximum sensitivity and specificity were 1 minute at 94° C. for initial denaturation, then forty-five cycles of three steps consisting of 0 second at 95° C., 5 seconds at 60° C. and 9 seconds at 72° C. Amplification was monitored during each elongation cycle by measuring the level of fluorescence, and after amplification, melting curve analysis was performed. With this assay, DNA from all prominent bacterial contaminants of platelet concentrates was extracted using RUCLANAP. Analytical sensitivity tests were performed on 9 frequent bacterial contaminants of platelets: *Enterobacter cloacae, Bacillus cereus, Salmonella choleraesuis, Serratia marcescens, Pseudomonas aeruginosa, Staphylococcus aureus, Staphylococcus epidermidis,*

*Escherichia coli* and *Klebsiella pneumoniae*. The detection limit was ≦20 CFU/mL of platelet concentrates for all of these 9 species tested.

Example 5

Use of RUCLANAP for the detection of group B streptococci in anal, vaginal, and combined vaginal/anal specimens. The development of conventional and real-time PCR assays for the rapid detection of group B streptococci was initially published in Clinical Chemistry, 2000, 46: 324-331. Subsequently, a clinical study based on these assays has been described in the New England Journal of Medicine, 2000, 343: 175-179. No information regarding the sample preparation protocol was disclosed in these publications. The efficacy of two polymerase-chain-reaction (PCR) assays for routine screening of pregnant women for group B streptococci at the time of delivery was studied. Anal, vaginal, and combined vaginal/anal specimens were obtained from 112 pregnant women; for 57 women, specimens were obtained before and after rupture of the amniotic membranes. The specimens were tested for group B streptococci (i) by culture in a standard selective broth medium, (ii) with a conventional PCR assay, and (iii) with a fluorogenic PCR assay.

The rapid lysis protocol used to prepare clinical samples for DNA amplification in these studies was the following:

A. The BBL Culturette™ swab (BD Microbiology Systems) used to sample anal, vaginal or vaginal-anal surfaces was inserted in a 1.5-mL, screw-capped microtube containing 300 μL GNS medium (Todd-Hewitt broth supplemented with 8 μg/mL of gentamicin and 15 μg/mL of nalidixic acid). The tip of the swab was rolled around the tube to expel the maximum of liquid.

B. A 10 μL aliquot was transferred to a 1.5-mL, screw-capped microtube containing 0.05 g of sterile, acid-washed glass beads (universal lysis mix, as described in Example 1), to which 40 μL of TE buffer were added. The microtube was vortexed for 5 min at speed level 7 on a Genie2 model vortex from Fisher Scientific.

C. After a quick centrifuge spin, the microtube was heated for 2 min at 95° C.

D. 1.5 μL of the mixture was used directly in the PCR reaction. Extracts could be stored for several months at −20° C. without any significant loss in PCR analytical sensitivity.

Based on culture, the combined vaginal/anal specimens from 33 of the 112 women (colonization rate of 29.5%) were positive for group B streptococci. The two PCR assays detected group B streptococcal colonization in specimens from 32 of these 33 women: the one negative PCR result was a sample obtained after the rupture of membranes. As compared with the culture results, the sensitivity of both PCR assays was 97.0% while the negative predictive value was 98.8%. Both the specificity and the positive predictive value of the two PCR assays were 100%. The length of time required to obtain results was 30 to 45 min for the fluorogenic PCR assay, 100 min for the conventional PCR assay, and at least 36 hours for the culture method.

Alternatively, the above protocol was also used in the following manner:

A. The BBL Culturette™ swab (BD Microbiology Systems) used to sample anal, vaginal or vaginal-anal surfaces was inserted in a 1.5 mL, screw-capped microtube containing 1 mL of TE buffer. The stem of the swab was wrapped in gauze and bent until it broke, so that the microtube containing the inoculated portion of the swab could be closed.

B. Cells were resuspended in solution by vortexing vigorously at least 15 seconds. A 50 μL aliquot was transferred to a 1.5-mL, screw-capped microtube containing 0.05 g of sterile, acid-washed glass beads (universal lysis mix, as described in Example 1). The microtube was vortexed for 5 min at speed level 7 on a Genie2 model vortex from Fisher Scientific.

C. After a quick centrifuge spin, the microtube was heated for 2 min at 95° C.

D. 1.5 μL of the mixture was used directly in the PCR reaction.

The efficiency of *Streptococcus agalactiae* lysis by the RUCLANAP method was estimated to 99.99%, as determined by viable counts.

Example 6

Application of RUCLANAP for direct detection of *S. saprophyticus* from urine samples. This assay was published in the Journal of Clinical Microbiology, 2000, 38: 3280-3284. No information regarding the sample preparation protocol was disclosed in this publication. *Staphylococcus saprophyticus* is one of the most frequently encountered microorganisms associated with acute urinary tract infections (UTIs) in young, sexually active female outpatients. Conventional identification methods based on biochemical characteristics can efficiently identify *S. saprophyticus*, but the rapidity of these methods needs to be improved. Rapid and direct identification of this bacterium from urine samples would be useful to accelerate the diagnosis of *S. saprophyticus* infections in the clinical microbiology laboratory. A PCR-based assay for the specific detection of *S. saprophyticus* has been developed. An arbitrarily primed PCR amplification product of 380 bp specific for *S. saprophyticus* was sequenced and used to design a set of *S. saprophyticus*-specific PCR amplification primers (SEQ ID NO. 1208 and 1209 in patent publication WO 01/23604). The PCR assay, which uses standard agarose gel electrophoresis for amplicon analysis, was specific for *S. saprophyticus* when tested with DNA from 49 gram-positive and 31 gram-negative bacterial species. This assay was also able to amplify DNA efficiently from all 60 strains of *S. saprophyticus* tested, which originated from various geographical areas. This assay was adapted for direct detection from urine samples.

The protocol used for the rapid lysis of bacterial cells for the release of nucleic acids from urine samples was the following: 500 μL of urine samples spiked with various amounts of *S. saprophyticus* cells were transferred to a 1.5-mL, screw-capped microtube containing 0.05 g of sterile, acid-washed glass beads (universal lysis mix, as described in Example 1). After centrifugation for 5 min at 15 800 g, the supernatant was discarded and the pellet was washed with 1 mL of PBS. After another centrifugation for 5 min at 15 800 g, the supernatant was discarded. Then, 50 μL of TE or PBS were added to the tube, and the sample was resuspended and lysed by vortexing for 5 min at speed level 7 on a Genie2 model vortex from Fisher Scientific. A heating step of 2 min at 95° C. followed. One μL of prepared urine sample was added directly to a PCR reaction. The analytical sensitivity levels achieved with RUCLANAP-treated urine samples were 0.3-1.4 CFU/PCR reaction with 40 cycles of amplification. By contrast, spiked urine samples added directly to the PCR (without treatment) showed a detection limit of 700-800 CFU/PCR. This PCR assay for the specific detection of *S. saprophyticus* is simple and rapid (approximately 90 min, including the approximately 10 minutes required for urine specimen preparation).

Example 7

Detection of *Candida albicans, Escherichia coli* and *Staphylococcus aureus* in blood samples. We devised a procedure to detect fungal and bacterial nucleic acids from infected blood. As blood contains large amounts of potent PCR inhibitors, rapid washes are required prior to the RUCLANAP protocol. Blood samples (1 mL) spiked with various amounts of bacterial or fungal cells were added to 1.5 mL microtubes containing glass beads for the universal or yeast lysis (Example 1). Three sequential washes were then performed by adding 1 mL of TE buffer to the tube and mixing briefly, with a centrifugation step (21 000 g for 1 min) and removal of the supernatant by aspiration between each wash. After the last wash, a quick centrifuge spin was performed and the residual liquid was removed by gentle aspiration. 12.5 µL of 5×TE buffer were added to the beads, and cells were then disrupted in the FastPrep® FP-120 apparatus for 45 seconds at power level 6. After a quick centrifuge spin, the microtube was heated 2 min at 95° C. and then centrifuged briefly. 2 to 4 µL of the preparation were used for PCR amplification. Using species-specific PCR assays described in our previous patent publication WO 01/23604, we obtained the following detection limits: 40 CFU/mL of blood for *Escherichia coli*, 30 CFU/mL of blood for *Staphylococcus aureus*, and 50 CFU/mL of blood for *Candida albicans*. Omission of the final heating step resulted in a loss in sensitivity, demonstrating that PCR inhibitors still present in washed blood samples can be successively eliminated by heat.

Example 8

RUCLANAP for extraction of human DNA from clinical samples. Although our goal is to detect DNA from microorganisms, human DNA is extracted as well from the clinical samples described in Examples 3 to 7, 11, 12, 15 and 17. For example, using primers specific to the β-globin gene (Swan et al., 1999, J. Clin. Microbiol. 37: 1030-1034), we could detect from 1 to 104 copies of this human genetic target in rectal swabs treated with RUCLANAP, as described in Example 12.

RUCLANAP cannot only be useful for genetic purposes, but is also useful to monitor the efficiency of the sampling procedure. The validity of individual samples can be monitored by measuring the human DNA load on the swab used for sampling, and comparing the result with a defined threshold.

Example 9

Effect of RUCLANAP on *Bacillus subtilis* endospores. Recovery of DNA from bacterial endospores has been described, but the tedious methods used in many studies resulted in severely sheared DNA, which hindered PCR sensitivity (Kuske et al., 1998, Appl. Environ. Microbiol. 64: 2463-2472). These authors have demonstrated that bead mill homogenization was the only effective method to extract DNA from bacterial endospore preparations. We demonstrate here the efficacy of RUCLANAP on spores.

The following protocol for endospore enrichment and purification was adapted from the method of Belgrader et al. (Analytical Chemistry 1999, 71: 4232-4236). A 50-mL culture of *Bacillus subtilis* grown in sporulation medium (Holt and Krieg, Enrichment and Isolation, In: Methods for General and Molecular Bacteriology, 1994, American Society for Microbiology, Washington, D.C.) was vortexed, then separated in two volumes of 25 mL. After centrifugation at 2500 g for 20 min, the pellets were washed three times with 5 mL of sterile distilled water, each wash being centrifuged at 2500 g for 10 min. The final pellets were resuspended in 4 mL of 50 mM NaCl, 100 mM EDTA, pH 6.9. Lysozyme was added at a final concentration of 1 mg/mL, and the mixture was incubated at 30° C. for 90 min. After two additional washes as described above, the pellets were resuspended in 1 mL of 5% Triton X-100.

Next. 250 µL of the above endospore suspension were submitted to buoyant density separation over 600 µL of PERCOLL™SIM-40 (40% PERCOLL™ density gradient media (Amershain Biosciences) and 60% peptone water (BD Microbiology Systems, Cockeysville, Md., USA)) in a 1.5 mL screw-capped microtube. The mixture was centrifuged 15 min at 750 g. The pellet was washed three times with 250 µL of sterile water, each wash being centrifuged at 9300 g for 2 min. The final pellet was resuspended in 100 µL of sterile distilled water. The final purified spore suspension was serially diluted 1/10 to a final factor of $1 \times 10^8$ 100 µL of each dilution were either plated onto blood agar plates for bacterial count, or placed in a hemacytometer for endospore count. The final purified spore suspension consisted of $1.73 \times 10^{10}$ endospores/mL, which corresponded to $5.7 \times 10^9$ CFU/mL.

The RUCLANAP method was adapted for endospore lysis in the following manner. A volume of 100 µL of each serial dilution of purified endospores was centrifuged 5 min at 9300 g, the pellet was resuspended in 40 µL of TE buffer, and transferred to a 1.5 mL screw-capped tube containing glass beads (universal lysis mix, see Example 1). Endospores were disrupted in the FastPrep® FP-120 apparatus for 45 seconds at power level 6. After a quick centrifuge spin, the microtube was heated for 5 min at 95° C. Subsequently, 100 µL of a 1/10 dilution of the lysed material was plated onto blood agar plates to assay endospore lysis. The efficiency of lysis of *Bacillus subtilis* endospores by RUCLANAP was estimated at 98.8% based on CFU counts performed before and after the lysis treatment.

One µL of a 1/10 dilution of the lysed material was used for PCR amplification. The PCR assay used for universal bacterial detection using primers SEQ ID NO. 643 and 644 has been described in our previous patent publication WO 01/23604.

The detection limit determined with untreated endospores was in the range of $1.3 \times 10^5$ to $1.7 \times 10^6$ endospores/mL, whereas the detection limit of endospores lysed with RUCLANAP was in the range of $1.3 \times 10^3$ to $1.7 \times 10^4$ endospores/mL (approximately 100 times better). In each PCR reaction tube, we could detect 3 to 43 RUCLANAP-treated endospores, compared to a detection limit of 320 to 4340 for untreated endospores. Further concentration of spore suspensions before RUCLANAP can allow to lower the detection limit in terms of CFU per mL.

Example 10

Detection of bacteria in bovine milk using RUCLANAP. Clinical mastitis is a common disease in dairy cows in Canada; approximately 1 in 5 lactating cows has at least one episode of clinical mastitis in its lifetime. As costs for each case are estimated to 150-200 $CAN, a crude estimate of losses to the Canadian dairy industry amounts to 44 million $CAN annually; in the U.S., the estimation is about $1.8 billion. The most common bacterial mastitis pathogens are *Staphylococcus* sp., *Streptococcus* sp., and coliforms (Sargeant et al., 1998, Can. Vet J. 39: 33-38). We have designed a protocol based on the RUCLANAP method to detect bacteria in bovine milk.

The milk samples were first incubated at 37° C. for 6 hours. The protocol, using PERCOLL™ density gradient media buoyant density separation, to extract nucleic acids from bovine milk was as described in Example 4, using a total weight 0.01 g of glass beads solely composed of the 150-212 µm size. A range of 80 to 100% of the milk samples positive by culture for *Staphylococcus aureas* or *Streptococcus agalactiae* were detected by our species-specific PCR assays targeting these two bacterial species (assays described in Examples 11 and 5, respectively).

Example 11

Use of RUCLANAP for the detection of *Staphylococcus aureus* in nasal swabs. One of the PCR assays described by Martineau et al. (2000, J. Antimicrob. Chemother. 46: 527-534) has been specifically used to detect *Staphylococcus aureus* from nasal swabs, using RUCLANAP to extract the nucleic acids. The protocol used was the following:
A. The BBL Culturette™ swab (BD Microbiology Systems) used to sample nasal mucosa was inserted into a 1.5-mL, screw-capped microtube containing 300 µL of TE buffer, supplemented with 1.5 mg/mL of BSA. The stem of the swab was wrapped in gauze and bent until it broke, so that the microtube containing the inoculated portion of the swab could be closed.
B. Cells were resuspended in solution by vortexing 1 min. A 50 µL aliquot was transferred to a 1.5-mL, screw-capped microtube containing 0.05 g of sterile, acid-washed glass beads (universal lysis mix, as described in Example 1). The microtube was vortexed for 5 min at speed level 7 on a Genie2 model vortex from Fisher Scientific.
C. After a quick centrifuge spin, the microtube was heated for 2 min at 95° C.
D. After a quick centrifuge spin, 2 µL of the mixture was used directly in the PCR reaction using the *Staphylococcus aureus*-specific PCR assay originally described by Martineau et al. (1998, J. Clin. Microbiol. 36:618-623). Extracts could be stored for several months at −80° C. without any significant loss in PCR sensitivity.

In a preliminary study with this PCR assay, 81 nasal swabs were processed using the RUCLANAP protocol. A total of 36 samples were culture-positive for *Staphylococcus aureus*, and 35 of those samples were detected by our PCR assay, for a sensitivity of 97.2%. The heating step was essential to remove PCR inhibitors present in the nasal samples.

Example 12

Direct detection of vancomycin-resistant enterococci from fecal samples using RUCLANAP. The increasing incidence of nosocomial vancomycin-resistant enterococci (VRE) outbreaks attests to the importance of early identification of VRE-colonized patients to prevent person-to-person transmission. Routine culture methods for the detection of VRE from stool or rectal samples are reliable, but require at least 2 to 4 days for completion. Therefore, we investigated the use of a PCR-based assay coupled with capture-probe hybridization as an alternative for rapid detection of VRE directly from fecal samples. The latter were collected during a VRE hospital outbreak in Quebec City in January 2000.

Fecal material from 533 stools or rectal swabs were analyzed by i) standard culture method using selective agar media and ii) our PCR assay coupled with capture-probe hybridization. The PCR assay was performed directly from the fecal material prepared with the RUCLANAP method, in a manner similar to that described in Example 3. For stools, a sterile swab was dipped into the sample, then transferred to a 1.5-mL screw-capped microtube containing 1 mL of TE buffer. The stem of the swab was wrapped in gauze and bent until it broke, so that the microtube containing the inoculated portion of the swab could be closed. Rectal swabs were directly transferred to a 1.5-mL screw-capped microtube in the same manner. Fecal material was resuspended in solution by vortexing vigourously for 1 min. A 50 µL aliquot was transferred to a 1.5-mL screw-capped microtube containing 0.05 g of sterile, acid-washed glass beads (universal lysis mix, as described in Example 1). Subsequently, the microtube was vortexed for 5 min at speed level 7 on a Genie2 model vortex from Fisher Scientific. After a quick centrifuge spin, the microtube was heated for 2 min at 95° C. Then, 2 µL of 1:2.5, 1:5 and 1:10 dilutions were used in PCR reactions. Extracts could be stored for several months at −80° C. without any significant loss in PCR sensitivity.

A multiplex PCR assay consisting of vanA- and vanB-specific primer pairs was developed and coupled with post-PCR hybridization using two capture probes targeting the respective vanA and vanB amplicons. Primers and probes used in this multiplex PCR assay are described in Example 23 of our previous patent WO 01/23604.

Twenty-nine specimens were positive for VRE (all *Enterococcus faecium*) based on culture. PCR detected 28 of the 29 culture-positive specimens of which i) 26 were positive for vanA, and ii) 2 were positive for both vanA and vanB. Among the culture-negative specimens, PCR detected one additional vanA-positive and 10 vanB-positive specimens. Overall, the multiplex PCR assay had a sensitivity of 96.6% and a specificity of 97.9%. This assay based on RUCLANAP extraction represents a promising and rapid screening test for the detection of VRE from fecal samples.

Example 13

Effect of variations in the ratios of glass beads sizes, or in total weight of beads, on RUCLANAP. In order to verify if modifications in a) the ratio of glass beads sizes or b) total weight of beads used in the universal lysis mix had an effect on the sensitivity of the PCR detection, the following experiments were designed and performed. First, different bead ratios were compared. In the universal lysis mix, the ratio of small beads (150-212 µm) to large beads (710-1180 µm) is 4:1, and there are 40 mg of small beads+10 mg of large beads per 1.5 mL reaction tube. Two other bead ratios were tested for comparison while keeping the total weight of beads to 50 mg:
   3.5:1.5 (35 mg of small beads+15 mg of large beads)
   4:1 (40 mg of small beads+10 mg of large beads, universal mix)
   4.5:0.5 (45 mg of small beads+5 mg of large beads).

Next, different combinations of small/large beads ratios and total beads weight were compared:
   1:1 (10 mg of small beads+10 mg of large beads, total 20 mg)
   2.5:1 (25 mg of small beads+10 mg of large beads, total 35 mg)
   4:1 (40 mg of small beads+10 mg of large beads, total 50 mg, universal mix)
   5.5:1 (55 mg of small beads+10 mg of large beads, total 65 mg).

Finally, different total weights of small beads only were tested: 20 mg, 35 mg, 50 mg, and 65 mg.

A volume of 50 µL of serial tenfold dilutions of a mid-log culture of *Streptococcus agalactiae* ATCC 13813 was added to the different mixes of beads. The microtube was vortexed for 5 min at speed level 7 on a Genie2 model vortex from Fisher Scientific. After a quick centrifuge spin, the microtube was heated for 2 min at 95° C. Then, 1.5 µL of the mixture was used directly in the PCR reaction, which was described in Example 5.

No significant difference in the analytical sensitivity was observed for all the above bead ratios and weights tested.

Example 14

The effect of the particle size on lysis efficiency. The effect of the particle size on lysis efficiency was also tested on *Candida albicans, Escherichia coli, Enterococcus faecalis, Staphylococcus aureus,* and *Micrococus luteus.*

Bacteria were grown on blood agar at 37° C. overnight. Yeasts were grown on Sabouraud at 30° C. overnight. Cells were resuspended in PBS in order to obtain $10^8$ cells per ml (for yeasts, a reading of 0.23 on a Dade Behring nephelometer (Deerfield, Ill., USA), and for bacteria, a reading of 0.08).

In order to evaluate the effect of particle size on the efficiency of lysis of microbial cells, various types and sizes of solid particules were tested: 0.2 g of glass beads from Sigma (<106 µm, 150-212 µm, 212-300 µm, 425-600 µm, or 710-1180 µm), 0.2 g of a mixture of all of the preceding glass bead sizes, or 0.2 g of Ottawa sand.

For yeasts, the best analytical sensitivity was obtained when using the biggest particles (710-1180 µm) as well as with the mixture of beads of all sizes. The next best results were obtained with sand, followed by beads of medium size.

For bacteria, small size beads of 150-212 µm as well as the mixture of all bead sizes yielded the best results. Again, sand was less efficient.

The results obtained suggest that for efficient microbial cell lysis, the use of beads of all sizes, or of at least two sizes selected within the ranges of about 710-1180 µm and about 150-212 µm, is required. These sizes (the whole range thereof or the two more specific ones) would allow a better reproducibility of the lysis method over Ottawa sand, because the latter may vary from lot to lot, ultimately affecting the efficiency of cell lysis and consequently the analytical sensitivity of the NAT assay.

Example 15

Effect on PCR of potentially inhibitory substances present in anal/vaginal samples. The use of RUCLANAP for the detection of group B streptococci (GBS) was described in Example 5. A number of substances having PCR inhibitory potential may be found in anal, vaginal or combined vaginal/anal samples upon sampling in pregnant women just before labor. Those substances include urine, amniotic fluid, blood originating from the umbilical cord, vaginal secretions, meconium, stools and lubricant (K-Y® lubricating jelly from Johnson & Johnson, Markham, Ont., Canada). In order to assess their inhibitory potential, swabs were dipped in several samples of each of these pure substances, and the RUCLANAP protocol described at the end of Example 5 was performed. The GBS real-time PCR assay was then performed with 1.5 µL of processed sample (pure or diluted 1:1 in ultrapure water) in the presence of 100 copies of the internal control template (Ke et al., 2000, Clin. Chem. 46: 324-331). Inhibition was assessed by comparing the fluorescence emitted by the internal control in the presence of each of thoses inhibitory substances relative to a negative control (no inhibitory sample added). For all substances tested, the real-time PCR fluorescent signal was equivalent to the signal of the negative control, showing that the RUCLANAP procedure is able to control efficiently various PCR inhibitory substances.

Example 16

Effect of bacterial density on RUCLANAP. To determine if the bacterial density may affect the efficacy of RUCLANAP, two protocols were tested. In the first protocol, serial dilutions were performed on the bacterial sample before lysis with RUCLANAP, while in the second protocol, the bacterial sample was undiluted but dilutions were performed on the lysed material. The starting sample was obtained by preparing a bacterial suspension in PBS, calibrated to obtain $10^8$ bacteria per mL, using *Staphylococcus aureus* colonies grown overnight on an agar plate.

Serial 1/10 dilutions of the suspension were made in PBS, until obtaining $10^3$ bacteria/mL. A volume of 100 µl of the initial suspension or of each ten-fold dilution was mixed with beads of sizes 150-212+710-1180 µm (universal lysis mix, see Example 1). The mixture was placed in the FastPrep® FP-120 apparatus, and shaken at speed 6 for 45 seconds. Lysed material from the initial suspension ($10^8$ bacteria per mL) was serially diluted (ten-fold dilutions) in TE buffer until a final dilution factor of 1/100 000 was obtained. A PCR was conducted with universal primers (as described in Example 12 from our previous patent WO 01/23604), using 1 µL of lysed sample (or diluted lysed sample).

There was no significant difference in the sensitivity between the two protocols, indicating that at least in the range tested here, the density of bacterial population in the test sample does not affect significantly lysis efficacy.

Example 17

Total RNA extraction from *Escherichia coli* using RUCLANAP. This experiment was designed to demonstrate that RNA, suitable for cDNA synthesis and amplification by RT-PCR, may be extracted from bacterial cells using RUCLANAP. RUCLANAP was adapted for RT-PCR by adding RNase inhibitor. A volume of 50 µL of broth culture of *E. coli* ATCC 25922 in mid-log phase of growth (O.D.$_{.600}$=0.5) was centrifuged in a 1.5 mL microtube containing the universal mix of beads, and the cell pellet was resuspended in 50 µL of 5×TE buffer containing 40 U of recombinant ribonuclease inhibitor (RNasin®, Promega). The basic RUCLANAP protocol was then followed (Example 1), using the universal lysis mix. Serial tenfold dilutions of the lysate were performed in TE buffer.

Next, 10 µL of diluted lysate was mixed with 10 µL of digestion buffer (20 mM Tris-HCl pH 8.0, 5 mM $MgCl_2$, 0.2 mM $CaCl_2$) and incubated for 1 min at 37° C., with either 10 U of DNase I (RNase-free, Roche), or 0.14 U of RNase A (DNase-free, Qiagen), or both enzymes DNase I and RNase A, or no enzyme at all. An enzyme inactivation step of 5 min at 95° C. followed for all conditions tested. One µL of treated lysate was then added to the RT-PCR or the PCR reaction.

The Superscript™ One-Step RT-PCR with Platinum® Taq from Invitrogen (Carlsbad, Calif., USA) was used according to the manufacturer's instructions, in a final volume of 50 µL. Both steps, reverse transcription and PCR, were performed successively in the same reaction tube. Primers targeting the tuf gene and specific to the Escherichia genus were used (SEQ ID. NO. 1661 and 1665 in patent WO 01/23604). cDNA synthesis was accomplished by a 30 min incubation at 50° C., followed by an initial denaturation step of 2 min at 94° C. For the subsequent PCR amplification, 40 cycles of 15 s at 94° C., 30 s at 56° C. and 30 s at 72° C. were performed, followed by a final extension of 2 min at 72° C. The amplified mixture was resolved by gel electrophoresis (2% agarose in TBE, containing 0.5 μg/mL of ethidium bromide) and visualized under 254 nm UV illumination.

To assay the effectiveness of the enzymes tested, a PCR using the same conditions as described above was run in parallel with the enzyme-treated samples. DNase I treatment sucessfully degraded all the DNA, as no amplifiable product was detected.

The detection limit of the RT-PCR of the DNase I-treated lysate (RNA only) was approximately 10 CFU per reaction. No signal was observed from samples treated with both RNase A and DNase I, thereby confirming that RNA was initially present in the lysate. Hence, one can conclude that RUCLANAP is thus a simple and effective method for the isolation from bacterial cells of total RNA that can succesively be used for cDNA synthesis.

Example 18

Extraction of genomic DNA from *Cryptospordium parvum* using RUCLANAP. The universality of RUCLANAP was further demonstrated by obtaining crude genomic DNA from the parasite *Cryptosporidium parvum*. Oocytes were collected by centrifugation and resuspended in 50 μL of 5×TE buffer. The basic RUCLANAP protocol (Example 1) was followed, using the yeast beads mix. One μL of a ten-fold dilution of the crude preparation provided the template for specific amplification of the elongation factor 1 gene, using as primers SEQ ID NO. 798-800 and 804-806 from our previous patent publication WO 01/23604. The expected PCR products were detected by agarose gel electrophoresis.

Example 19

Extraction of genomic DNA from *Mycobacterium smegmatis* using RUCLANAP. Another example of the universality of RUCLANAP is the isolation of crude genomic DNA from difficult to lyse *Mycobacterium smegmatis*. Robson et al. (U.S. Pat. No. 5,376,527) have shown that cellular lysis of mycobacteria may be obtained by exposing the bacteria to a lysis-effective amount of heat, ranging from 2 to 20 minutes. Subsequently, DNA was further purified by phenol/chloroform extraction and ethanol-precipitated, which is much more cumbersome than the RUCLANAP method. Also, results showed that this method was not sensitive enough for detection directly from clinical samples without prior growth enrichment. For some mycobacterial species, the heating steps included in the PCR protocol were sufficient to release amplifiable target DNA, but this quick method was not universal for all Mycobacterium species tested.

The basic RUCLANAP protocol was used with the universal lysis mix (Example 1). Starting from a 0.5 MacFarland suspension in PBS of *M. smegmatis* prepared from colonies, cells (50 μL) were collected by centrifugation for 5 min at 21 000 g, the supernatant was discarded and the pellet was resuspended in 50 μL of 5×TE buffer. After RUCLANAP, one μL of serial ten-fold dilutions of the crude lysate provided the templates for specific amplification of the atpD gen, using a primer pair described in our previous patent publication WO 01/23604 (SEQ ID NO. 566 and 567). The unlysed cell suspension was also serially diluted ten-fold in PBS, and 100 μL from dilutions $10^{-5}$ and $10^{-6}$ were plated onto blood agar plates in triplicate to determine viable counts. One μL of each dilution of the unlysed cell suspension was also used as template in the PCR assay.

The unlysed cell suspension showed a count of $3.1 \times 10^4$ CFU/μL. No DNA amplification from all dilutions of the untreated cells suspension was detected by standard agarose gel electrophoresis, including the lowest dilution tested which contained $3.1 \times 10^4$ CFU/PCR reaction. On the other hand, the RUCLANAP-treated *M. smegmatis* cells were detected with a sensitivity limit of 3 CFU/PCR reaction. Treatment of the mycobacterial cells improved the detection by at least 10 000-fold. RUCLANAP is thus a rapid and sensitive method to detect hard to lyse *Mycobacterium smegmatis*.

Example 20

RNA extraction from HIV-1 using RUCLANAP. A variation from the basic RUCLANAP protocol was designed to extract RNA from type 1 human immunodeficiency virus (HIV-1) for comparison with the RNA extraction method of NUCLISENS™ nucleic acid HIV QT assay from Organon Teknika. This commercially available kit measures quantitatively HIV-1 RNA in human serum and plasma. The RNA extraction process is derived from the methodology of Boom et al. (J. Chit Microbiol., 1990, 28: 495-503); although effective, the assay is fastidious, time-consuming (a few hours) and requires the use of the toxic substance guanidine thiocyanate.

Starting from 500 μL of human plasma with a known HIV-1 viral load, both RNA extraction methods were compared. The NUCLISENS™ nucleic acid HIV QT assay was performed as described in the manufacturer's instructions. For RUCLANAP, 500 U of RNASIN® Ribonuclease inhibitor (Promega) were added to the sample. After a 5 min centrifugation at 21 000 g, the pellet was washed with 1 mL of 10 mM Tris-HCl, pH 8.0. After another centrifugation step in the same conditions and removal of the supernatant, the following were added: 0.2 g of beads (106 μm and finer, cat. no. G-4649, Sigma; presumably 75 μm-106 μm), 20 μL of RNA calibrators solution (see below), 10 μL of a 1% Triton X-100 solution, and 40 U of RNASIN® Ribonuelease inhibitor. Viruses were disrupted in the FASTPREP® FP-120 apparatus for 45 seconds at power level 6. A final quick spin at 10 000 g for 2 min followed.

Amplification and detection of extracted RNA obtained from either method was performed on the NUCLISENS™ nucleic acid Reader (Organon Teknika), according to the manufacturer's instructions. The technology used for amplification was NASBA (nucleic acid sequence-based amplification), which relies on the simultaneous activity of 3 enzymes: AMV-RT (Avian Myoblastosis Virus-Reverse Transcriptase), RNase H and $T_7$ RNA polymerase. Copies of the target RNA sequence and of the calibrators (3 artificial control RNAs) are synthesized by phage $T_7$ polymerase via an intermediate DNA molecule harboring the double-stranded $T_7$ RNA polymerase promoter. Detection of products relies on electrochemiluininescence (ECL) technology, Using either viral RNA extraction method, similar levels of recovery were obtained, demonstrating the universality of the RUCLANAP method. Furthermore, RUCLANAP was more rapid, and simpler to use than the RNA extraction method of the NUCLISENS™ nucleic acid HIV QT assay. The universal mixture 150-212 μm: 710-1180 μm (4:1) could be used per se or adapted to lyse viruses (by adding smaUer particles, namely in the 75-106 μm range, by reducing the proportions of large beads or by providing a separate composition of small particles only (about 150 μm or lower, namely 100 μm or lower)).

Example 21

Use of zirconia beads for RUCLANAP. The basic RUCLANAP protocol was used with the universal lysis mix (Example 1), or with 0.05 g of 100 μm zirconia/silica beads (cat. no. 11079101z, BioSpec). A negative control, with no beads in the microtube, was also performed. Starting from a 0.5 MacFarland suspension in PBS of *Staphylococcus aureus* ATCC 25923 prepared from colonies, cells (100 μL) were collected by centrifugation for 5 min at 21 000 g, the supernatant was discarded and the pellet was resuspended in 100 μL of 5×TE buffer. After RUCLANAP, one μL of serial tenfold dilutions ($10^0$ to $10^5$) of the crude lysates obtained in the three different conditions was used as template in the *S. aureus*-specific assay described by Martineau et al. (2000, J. Antimicrob. Chemother. 46: 527-534). Amplification was detected by standard agarose gel electrophoresis. The unlysed cell suspension was also serially diluted ten-fold in PBS, and 100 μL from dilutions $10^{-5}$ and $10^{-6}$ were plated onto blood agar plates in triplicate to determine CFU counts.

The unlysed cell suspension showed a count of $3.5 \times 10^4$ CFU/μL. The detection limit for the negative control (no beads) was 350 CFU/PCR reaction. By contrast, the detection limit for RUCLANAP-treated *S. aureus* cells (using either the universal mix of glass beads or zirconia/silica beads) was 3.5 CFU/PCR reaction. Thus, RUCLANAP treatment of the staphylococcal cells improved the nucleic acid detection by at least 100-fold, and the method may be adapted to different types and sizes of beads.

Although the present invention has been described hereinabove by way of preferred embodiments thereof, it can be modified, without departing from the spirit and nature of the subject invention as defined in the appended claims.

The invention claimed is:

1. A method for the universal release of nucleic acids from viral particles, bacterial cells, yeast cells, fungal cells, parasitical cells, animal cells or human cells of a sample, suitable for use in a nucleic acid testing (NAT) assay, consisting essentially of the steps of:
   a) contacting the cells or viral particles with a mixture of at least a first set and a second set of solid lysing particles, wherein the particles in the first set are of a smaller diameter than the particles of the second set, and wherein the diameters of the first set fall between about 75 μm to about 212 μm and wherein the diameters of the second set fall between about 425 μm and 2000 μm, wherein the mixture does not contain any lysogenic agents,
   b) applying a mechanical force sufficient to lyse the cells or viral particles, so as to obtain a cellular or viral lysate; and
   c) controlling the presence and/or activity of nucleic acids testing (NAT) assay inhibitors.

2. The method of claim 1, wherein said first set and said second set of lysing particles fall within the range of about 150 μm to about 1500 μm in diameter.

3. The method of claim 1, wherein the said first set and said second set of lysing particles fall within the range of about 150 μm to about 1200 μm in diameter.

4. The method of claim 1 wherein the step of controlling NAT assay inhibitors is performed by either,
   a) removing the inhibitors out of the sample and/or the lysate;
   b) diluting the inhibitors in the sample and/or the lysate;
   c) inactivating the inhibitors in the sample and/or the lysate; or
   d) any combination of (a)-(e).

5. The method of claim 4, wherein the step of removing the inhibitors is a step of adsorbing said inhibitors out of the sample or the lysate.

6. The method of claim 5, wherein the step of adsorbing is performed with activated carbon.

7. The method of claim 4, wherein the step of removing the inhibitors is a step of purifying the cells, viral particles, or cellular components on a density gradient.

8. The method of claim 4, wherein the step of removing the inhibitors is a step of or a repetition of the steps of centrifuging and washing the cells, viral particles, or the cellular components.

TABLE 1

Efficiency of DNA recovery using the RUCLANAP and 8 commercial kits.

DNA EXTRACTION KITS AND METHODS[a]

| Microbial species | RU-CLANAP | DYNA-BEADS ® | FAST RNA ™ Kit | ISTA-GENE ™ | HIGH PURE ™ PCR Template Kit | NUCLI-SENS ™ | QU-IAAMP ® Tissue Kit | FAST DNA ™ Kit | GENE RELEAS-ER ™[b] |
|---|---|---|---|---|---|---|---|---|---|
| E. coil | ref | −1 | −1/2 | −1/2 | 0 | −1/2 | 0 | 0 | — |
| S. aureus | ref | −3 | −1/2 | −2 | −1 | −2 | −2 | −4 | — |
| E. faecium | ref | −3 | −1 | −3 | 0 | −4 | −1 | −3 | — |
| C. albicans | ref | −2 | 0 | 0 | −1 | −3 | 0 | 0 | — |
| Total[c] | 0 | −9 | −2 | −5,5 | −2 | −9,5 | −3 | −7 | — |

[a]The efficiency of DNA recovery was evaluated by d3etermining the highest ten-fold dilution of each DNA preparation detectable by PCR. The detection limit is expressed in Δlog, using the RUCLANAP as reference (ref): negative values indicate lower DNA yields while positive values indicate higher DNA yields.
[b]The GENERELEASER ™ kit could not be evaluated because of heavy contamination of the reagents by bacterial DNA.
[c]Total represents the total number of Δlogs in analytical sensitivity as compared to RUCLANAP.

9. The method of claim 4, wherein the step of inactivating the inhibitors is a step of heating the sample or the lysate.

10. The method of claim 9, comprising the step of heating to a temperature from about 55° C. to about 100° C. and a time of heating from about 15 seconds to about 15 minutes.

11. The method of claim 4, wherein said first set and said second set of lysing particles fall within the range of about 150 μm to about 1200 μm in diameter.

12. The method of claim 1, wherein said first set of lysing particles have diameters in the range of about 150 μm to about 212 μm and said second set of lysing particles have diameters in the range of about 710 μm to about 1180 μm.

13. The method of claim 12, wherein the ratio (w/w) of said lysing particles having a diameter size between about 150 μm and about 212 μm to said lysing particles having a diameter size between about 710 μm and 1180 μm is 4:1.

14. The method of claim 1, wherein the particles are spherical.

15. The method of claim 1, wherein said solid particles are composed of zirconium.

16. The method of claim 1, wherein said solid particles are composed of silica.

17. The method of claim 1, wherein the ratio (w/w) of total particles to sample is between about 4:1 and about 1:2.

18. The method of claim 1, wherein said contacting step is carried out in the presence of a chelating agent.

19. The method of claim 18, wherein said chelating agent comprises 1 to 5 mM EDTA.

20. The method of claim 1, wherein said contacting step is carded out in the presence of a a buffering agent.

21. The method of claim 20, wherein said buffering agent comprises 10 to 50 mM Tris-HCl (pH 8.0).

22. The method of claim 1, wherein the sample comprises viruses, bacterial cells, yeast cells, fungal cells, parasitical cells, animal cells, human cells, or any combination thereof.

23. The method of claim 1, for the release of nucleic acids from yeast cells, wherein said second set of lysing particles falls within the range of about 710 μm to about 1180 μm in diameter.

24. The method of claim 1, wherein said first set of lysing particles fall within the range of about 150 μm to about 212 μm in diameter.

25. The method of claim 1, wherein said first set of lysing particles fall within the range of about 75 to about 106 μm in diameter.

26. The method of claim 1, wherein step (b) is performed within 5 minutes.

27. The method of claim 1, wherein said mixture of lysing particles does not comprise non-lysing particles greater than 2 mm.

28. A composition of matter for the universal release of nucleic acids from viral particles, bacterial cells, yeast cells, fungal cells, parasitical cells, animal cells or human cells of a sample, suitable for use in a nucleic acids testing (NAT) assay, consisting essentially of a mixture of solid lysing particles, with a mixture of at least a first set and a second set of solid lysing particles, wherein the particles in the first set are of a smaller diameter than the particles of the second set, and wherein the diameters of the first set fall between about 75 μm to about 212 μm and wherein the diameters of the second set fall between about 425 μm and 2000 μm, and wherein the mixture does not contain any lysogenic agents.

29. The composition of claim 28, wherein said first set and said second set of lysing particles fall within the range of about 150 μm to about 1500 μm in diameter.

30. The composition of claim 28, wherein said first set and said second set of lysing particles fall within the range of about 150 μm to about 1200 μm in diameter.

31. The composition of claim 28, wherein said first set of lysing particles have diameters in the range of about 150 μm to about 212 μm and said second set of lysing particles have diameters in the range of about 710 μm to about 1180.

32. The composition of claim 31, wherein the ratio (w/w) of said lysing particles having a diameter size between about 150 μm and about 212 μm to said lysing particles having a diameter size between about 710 μm and 1180 μm is 4:1.

33. The composition of claim 28, wherein said solid particles are composed of zirconium.

34. The composition of claim 28, wherein said solid particles are composed of silica.

35. The composition of claim 28, which comprises 0.02 g to 0.2 g of said solid particles, and wherein said sample volume is 10 μL to 500 μL.

36. The composition of claim 28, which further comprises a chelating agent.

37. The composition of claim 36, wherein, said chelating agent is in an amount achieving a final concentration of 1 to 5 mM EDTA.

38. The composition of claim 28, which further comprises a buffering agent.

39. The composition of claim 38, wherein said buffering agent comprises 10 to 50 mM Tris-HCl (pH 8.0).

40. The composition of claim 28, wherein said second set of lysing particles fall with the range of about 710 μm to about 1180 μm in diameter.

41. The composition of claim 28, wherein said first set of lysing particles fall within the range of about 150 μm to about 212 μm in diameter.

42. The composition of claim 28 wherein said first set of lysing particles fall within the range of about 75 μm to about 106 μm in diameter.

43. The composition of claim 28, which further comprises a material binding or adsorbing NAT assay inhibitors.

44. The composition of claim 43, wherein said material is activated carbon.

45. The composition of claim 28, wherein said mixture of lysing particles does not comprise non-lysing particles greater than 2 mm.

* * * * *